United States Patent [19]
Dardik et al.

[11] Patent Number: 5,131,908
[45] Date of Patent: * Jul. 21, 1992

[54] TUBULAR PROSTHESIS FOR VASCULAR RECONSTRUCTIVE SURGERY AND PROCESS FOR PREPARING SAME

[76] Inventors: Herbert Dardik, 270 Highwood Ave., Tenafly, N.J. 07670; Irving I. Dardik, Hillcrest Rd., Great Meadows, N.J.

[*] Notice: The portion of the term of this patent subsequent to Feb. 5, 2008 has been disclaimed.

[21] Appl. No.: 622,338

[22] Filed: Nov. 23, 1990

Related U.S. Application Data

[63] Continuation of Ser. No. 434,939, Nov. 9, 1989, abandoned, which is a continuation of Ser. No. 91,661, Sep. 1, 1987, abandoned.

[51] Int. Cl.⁵ .............................................. A61F 2/06
[52] U.S. Cl. ........................................ 600/36; 623/66; 623/1
[58] Field of Search ................ 600/36; 606/158, 191, 606/194; 8/94.1 R, 94.11, 94.19 R

[56] References Cited

U.S. PATENT DOCUMENTS

| | | | |
|---|---|---|---|
| 3,966,401 | 6/1976 | Hancock et al. | 8/94.11 |
| 3,974,526 | 8/1976 | Dardik et al. | 623/1 |
| 4,990,131 | 2/1991 | Dardik et al. | 8/94.11 |

Primary Examiner—Randy C. Shay
Assistant Examiner—Gina Gualtieri
Attorney, Agent, or Firm—Rosen, Dainow & Jacobs

[57] ABSTRACT

Arteries and veins of umbilical cords are treated by processes described, fitted with a biodegradable mesh support and used as tubular prosthesis for vascular reconstructive surgery.

20 Claims, 1 Drawing Sheet

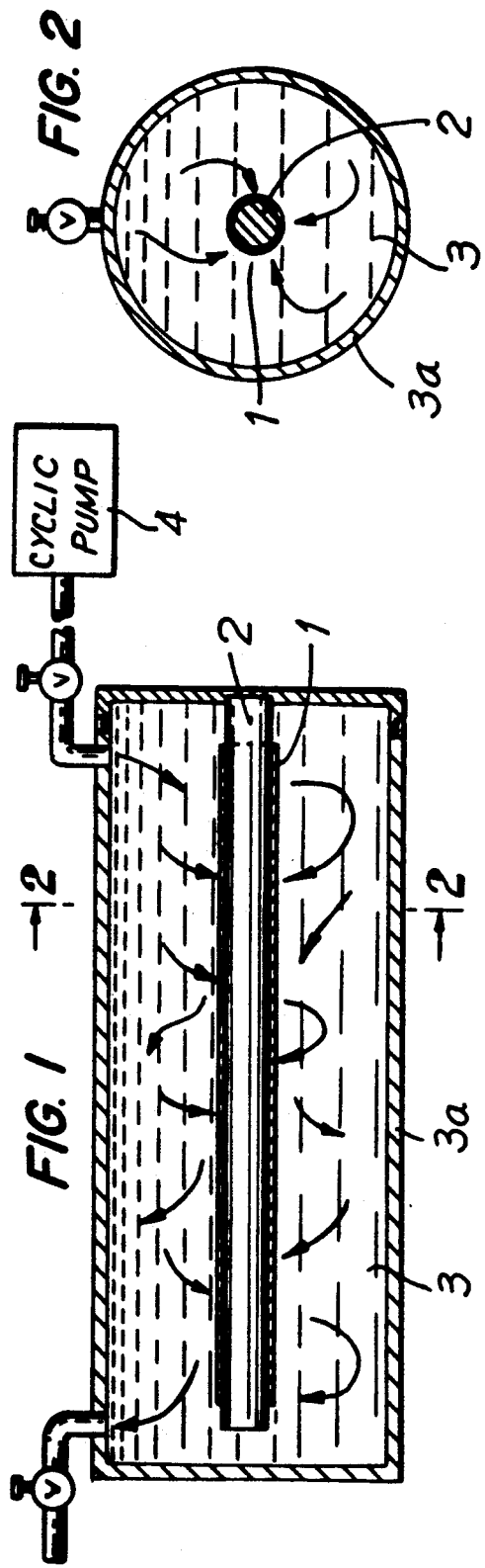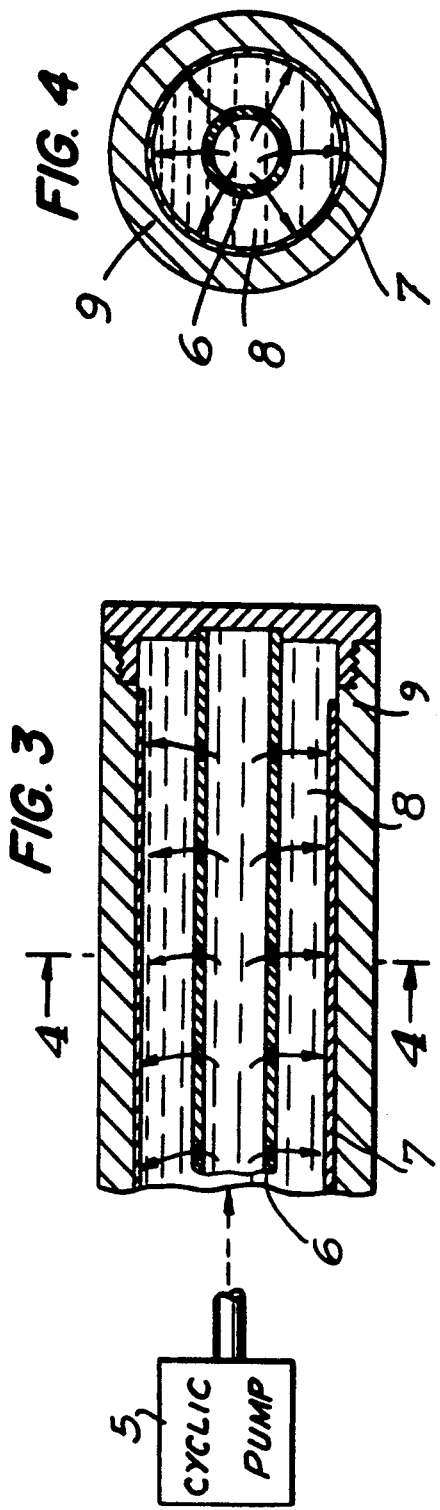

TUBULAR PROSTHESIS FOR VASCULAR RECONSTRUCTIVE SURGERY AND PROCESS FOR PREPARING SAME

This application is a continuation of application Ser. No. 07/434,939 filed Nov. 9, 1989, abandoned, which is a continuation of Ser. No. 91,661 filed Sep. 1, 1987, now abandoned.

The present invention relates to new and useful improvements in tubular prostheses for vascular reconstructive surgery from the veins and arteries of the human umbilical cord.

BACKGROUND OF THE INVENTION

The search for the ideal blood vessel substitute has to date focused on biological tissues and synthetics. Variations upon simple substitutions with these materials have included such innovations as heparin bonding, endothelial coating with cells grown in tissue culture, and in vivo collagen tube formation on silicone mandrels. Despite intensive efforts to improve the nature of blood vessel substitutes many problems remain, such as increasing failure rate with decreasing caliber of the blood vessel substitute, a high failure rate when infection supervenes, biological failure or degradation by fibrin layering, intimal and subintimal hyperplasia, and aneurysm formation.

A major problem in vascular reconstructive surgery is how to effectively supply blood to organs and tissues whose blood vessels are inadequate either through congenital defects or acquired disorders such as trauma, arteriosclerosis and other diseases. Various techniques and materials have been devised to excise and replace blood vessels, to bypass blood vessels, and to patch, i.e., widen the channels of vessels. Initially, arterial homografts (human arteries) were used to restore continuity; however, limited supply, inadequate sizes, development of aneurysms and arteriosclerosis necessitated the search for a better substitute.

A great advance was the development of the partially porous and pliable synthetic plastic cloth. Synthetic fibers frequently used as graft material include polyethylene terephthalate (Dacron ®) and polytetrafluoroethylene (Teflon ®). Some of the problems experienced with the use of artificially constructed grafts include: (1) infection leading to hemorrhage, sepsis and/or death; (2) the inner lining of the graft is thrombogenic, so that it is predisposed to clotting which may result in total occlusion of the graft and distal embolism of the clot; (3) the rigidity of fabric grafts may result in twisting and kinking especially where a joint is crossed leading to graft occlusion; (4) because of clotting difficulties, smaller caliber artificial grafts are frequently unsuccessful. Grafts smaller than about 5 mm in inside diameter almost invariably becomes blocked by clots which form therein, and clotting difficulties arise in certain bodily locations even with vascular grafts having inside diameters as great as 10 mm. Moreover, a delicate balance must be struck in the porosity of the synthetic graft since the wall thereof must be sufficiently porous to permit ingrowth and deposition of fibrin so that eventually the wall is covered with scar tissue both internally and externally and yet not be so porous that hemorrhage occurs. This makes it necessary to pre-clot the knitted graft prior to use. Many problems posed by artificially manufactured prostheses have led investigators to seek newer and better methods. These include new techniques of "cleaning out" an artery such as by carbodissection, dilating arteries, development of bovine heterografts, and creating collagen tubes by inserting a mandrel within the recipient for later use of a graft.

It is known that homografts have been used for vascular grafting with considerable success. Commonly, the saphenous vein has been used in cases where the patient is the donor (an autograft) and where another human is a donor (allograft). These vessels require no treatment before implantation; however, they present problems of unavailability, disparity in size, nonuniformity of caliber, presence of valves and varicosities, and the need for additional authorization in the case of allografts. The removal of the saphenous vein to be used for vascular grafting in the same patient involves keeping the patient on the operating table for a substantially longer time. Moreover, the operation is quite delicate and sometimes is a failure. Finally, where rejection is a problem and the patient needs further grafting after the patient's own saphenous veins have been removed, repair by this method becomes impossible.

In a prior invention of applicant, a combined biologicsynthetic vascular graft consisting of umbilical cord vessels surrounded by a synthetic mesh support is provided. The vessels in the human umbilical cord are separated, treated according to the process described in U.S. Pat. 3,974,526 and used as grafts in vascular reconstructive surgery.

Traditionally discarded after division from the infant at birth, the umbilical cord here has found a new use as the source of valuable grafting materials. It is composed of a vein and two arteries surrounded by a sticky jelly-like substance called Wharton's jelly all encased in the surrounding tissue. The cord varies in length from inches to over three feet in length and is highly flexible. Both the arteries and veins contained therein are suitable for use in vascular surgery. The umbilical cord is fetal tissue in a primitive state giving it the advantage that antigenicity is lower than in adult tissue.

The umbilical cord may be used fresh or it may be preserved for future use. The cord may be freeze-dried, refrigerated, chemically stored or preserved in other known ways. It may require treatment with antibiotics, chemicals, drugs, X-rays and temperature to insure that it is sterile when ready for use. It is antigen and may require chemical or other known treatment to remove any antigen substances. Coiled at the time of delivery, the cord can be straightened out by mechanical or chemical techniques. Cords obtained from mammals, premature babies, early or terminated pregnancies can also be used to repair smaller vessels.

Until the above-noted discovery, the unique morphology of umbilical cord vessels appeared to render them unsuitable grafting materials. The one vein and two arteries in these cords are located together within the protective tissue of the cord; the arteries spiral around the vein in a helical fashion, an occurrence unique in vascular anatomy. This arrangement apparently results in reduced kinking and twisting. Once separated and treated according to the process described in U.S. Pat. No. 3,974,526, the vessels are straight yet remain flexible. They can be shaped to meet the specific needs of the recipient by adjusting the width and length. The grafts as prepared can be used as both arterial and venous substitutes; furthermore, they can be used to patch and repair diseased vessels of the body. Finally, it should be noted that the availability of umbilical cords represents a virtually unlimited supply of grafting material in connection with the present invention.

The umbilical cord vessels, especially the arteries, frequently contain valves known as the valves of Hoboken. The presence of these "valves" is one of the factors which has made it unobvious to previous investigators to use these vessels as tubular grafts. Within the present process of preparing a cord for prosthetic use, the valves are treated and eliminated so as to create an unconstricted inner surface within the vessels.

The vessels used as grafts herein are commonly three feet in length thereby eliminating the need for joining several shorter grafts often necessary in vascular surgery involving the arteries or veins of the leg. The diameter of the vessel can also be adjusted by shrinking the vessel during the preparation process and the wall thickness of the vein can also be controlled during the separation step by the amount of tissue removed. The tubes may be slit open longitudinally to obtain a planar graft or patch for repairing vessels of the body. The grafts may be tapered to closely conform in shape to the body's natural vessels.

Tapering also eliminates a major problem associated with autogenous vein grafts as arterial substitutes. Since the saphenous vein contains valves which direct blood flow toward the heart, these grafts must be reversed when used to replace an artery, resulting in a graft which is tapered in the opposite direction to that of the original or host vessel. The graft of applicant's invention is valveless and readily can be shaped and tapered to the recipient's needs. The need for additional operations, as in the use of autogenous vein grafts such as the saphenous vein, is obviated by the use of these umbilical cord grafts. Such operations to obtain the patient's own vein involve the added risks of prolonged anesthesia, infection, disease and death to the donor.

The advantages of using umbilical cord veins and arteries as vascular grafts may be summarized as follows:

1) availability of grafting material which usually is obtained under sterile conditions (i.e. the operating room at delivery time);

2) ability to be shaped and tapered;

3) absence of valves or branches;

4) flexibility such that the graft can be used across joints;

5) low antigenicity which can be eliminated by the process;

6) use in small vessels without leading to thrombosis;

7) these thin-walled porous vessels permit hardening and tanning agents to penetrate easily during processing; and 8) the graft is entirely preformed, complete when implanted, and may contain an outer mesh support which allows for easy ingrowth of extra fibrocollagenous tissue from outside the graft.

The process in applicant's U.S. Pat. No. 3,974,526, eliminates antigenicity, hardens and strengthens the graft, removes the valves of Hoboken and any varicosities in the vessels, and shapes the vessel to any shape desired. The graft obtained is straight, flexible and can be twisted in any direction. This is a major advantage over autogenous vein grafts which must be implanted in their original shape to avoid minor twists which can lead to closure of the vessel when blood begins to flow through.

Finally, the use of the veins and arteries of the umbilical cord as vascular substitutes has the following advantages during surgical implantation:

1) operating room time (of autografts for example) can be reduced by one to two hours since the need for multiple incisions and the attendant additional procedures are eliminated;

2) a suitable tapered diameter makes it easy to implant the vessel to fit the host vessel to which it is attached;

3) the graft is sutured easily and with a minimum bleeding from the needle insertion hole;

4) the lumen of the graft following treatment remains open and does not collapse as does the saphenous vein; and 5) a needle can be inserted into the interstices of the mesh support without harming the graft.

A process for producing a tubular prosthesis for vascular reconstructive surgery, of the type described in U.S. Pat. No. 3,974,526 comprises the following steps: (a) cleansing the veins and arteries of the umbilical cord to remove blood and residual fluids; (b) removing Wharton's jelly from within the cord; (c) mechanically separating the two arteries and vein from the cord and from one another; (d) eliminating the valves of Hoboken within the vessel; (e) inserting a mandrel to shape the vessel; (f) treating the vessel with a hardening or tanning agent; (g) treating the vessel with an antithrombogenic agent; (h) applying a mesh support externally to the vessels; and (i) implanting the graft so formed.

The prosthesis produced according to this process is intended for use in vascular reconstructive surgery of animals including humans, primates and mammals. It may be used to repair, replace or augment a diseased or defective vein or artery of the body. The thin walled graft may be used as a substitute for the ureter, bile duct and other organs of the body.

Cleansing, rinsing or irrigating solutions which may be employed include water, sterile saline solution, Ringer's lactate solution, hydrogen peroxide, sodium bicarbonate solution, alcohol, and transplantation perfusate solutions.

Antithrombogenic agents which may be used to treat the graft include L-sodium glutamate, L-alanine, L-phenylalanine, L-cysteine, L-lysine.

Wharton's jelly may be removed mechanically or chemically using hyaluronidase to dissolve the hyaluronic acid which comprises the jelly.

The arteries are separated from the cord by passing an instrument between the arteries and the outer cord tissue. To separate the vein from the umbilical cord, a mandrel is inserted through the lumen of the vein and said mandrel is fixed in a vise like mechanism which permits rotation of the cord in order to separate the arteries which are spirally around the vein. The valves of Hoboken are eliminated by forcing a fluid through the lumen of the vein or artery. The fluid may be Ringer's lactate solution, gluteraldehyde, sterile saline solution, water or transplantation perfusate solution.

The mandrel inserted to shape the vessels and remove the remaining valves of Hoboken may be constructed of an inert material which will not react with the graft vessel or chemicals used in the process. For these purposes glass, silicone, stainless steel or plastic may be used. The mandrel may be straight or curved, solid or hollow, cylindrical or tapered, and smooth or perforated on its surface.

Hardening or tanning agents which may be used to shrink, dilate or otherwise shape the vessel include aldehydes such as glutaraldehyde, dialdehyde starch and formaldehyde, hydrous alcohol, glyoxal, and chronic oxide.

The mesh support applied to the shaped graft in Applicant's U.S. Pat. No. 3,974,526, may be made of any non-adsorbable synthetic material such as Dacron®, Teflon®, polyester, polypropylene, Mersilene mesh, plastic and cloth. The mesh is intended to provide support for the graft and should not be absorbed by it or the recipient host tissue readily. The material used must be sterile when implanted.

SUMMARY OF THE INVENTION

This invention is an improved process for producing tubular prostheses from umbilical cords for use in vascular reconstructive surgery and for the resulting improved prostheses.

Umbilical cord prostheses in vascular reconstructive surgery are required during their operative use to withstand pulsatile pressure. While umbilical cord prostheses have demonstrated a remarkable ability to maintain artificial arterial graft patency and function for protracted periods of time under these stressful conditions, it has sometimes been found that complications or problems arise with regard to long term implantation. The problems include biodegradation of the umbilical cord prosthesis manifested by graft dilatation, aneurysm formation and, in some instances, even dissolution of the graft material. Follow-up examinations of umbilical cord prostheses patients reveals that of those who survive five or more years, fifty percent or more of the grafts are either dilitated or have formed aneurysms.

Applicant believes that this degeneration of the umbilical cord vessel prosthesis is due in large measure to the reversal of aldehyde crosslinkages which interbond the collagen macromolecules of the umbilical cord vessel. While exact measurements are not available, the dissolution of these intermolecular aldehyde crosslinkages between adjacent collagen molecules is believed to occur as a function of time and pressure. The age of the graft and the pulsatile stresses it is subjected to as a vascular substitute are apparently detrimental prosthesis. Pathological changes in the cellular structure of the graft where the tanning process may have been incomplete also contribute to the deterioration of the graft.

This invention is directed to the improvement of a process for preparing an umbilical cord vascular prosthesis for use in surgery, using techniques as described below to enhance complete aldehyde crosslinkage between adjacent collagen molecules of the cord tissue and thereby reduce post-implantation changes in the graft. This invention comprises improvements in applicants' prior process for chemically and structurally modifying the veins and arteries of human umbilical cords to obtain vascular grafting material which is superior to existing blood vessel substitutes.

As described in applicants' previous patents, after removing the internal veins and arteries of the umbilical cord from its outer tissue and separating these vessels from one another, the vessels are treated with cleansing and tanning agents to eliminate antigenicity. A tanning or hardening solution, usually of gluteraldehyde in concentrations of between 0.15% and 1.0% fixes the vessel in the shape of the mandrel or mold inserted in the tubular prostheses while adding strength to the graft. It has been found that at lower concentrations gluteraldehyde solution does not render the graft non-antigenic, while at higher concentrations the reaction is too rapid and causes the walls of the vessel to become brittle, thus losing its flexibility and resilience. Accordingly, the obvious approaches using higher and lower concentrations failed to solve the problem and in fact caused other worse problems. The problem, more specifically, was to provide a prosthetic vessel free of antigenicity which retained its flexibility and strength, but yet avoided long-term deterioration due to reversal of aldehyde crosslinkages between adjacent collagen molecules of the umbilical cord vessel.

According to the present invention, the foregoing advantages are obtained and disadvantages avoided by treating the veins and arteries located within the human umbilical cord in the manner described herein. The new process for producing a tubular prosthesis for vascular reconstructive surgery comprises some or all of the following steps: (a) cleansing the umbilical cord; (b) mechanically removing extraneous outer tissues from the outer surface of the vein; (c) establishing and maintaining a minimum bore dimension of the vein; (d) treating the vein by contacting same with a tanning agent under cyclic pressure, where the pressure of the tanning fluid upon the cord is within the range of the pressure the cord vessel will experience as a human arterial prosthesis; (e) treating the vein with an antithrombogenic agent; (f) applying a biodegradable mesh support externally to the cord vein prosthesis; and (g) implanting the graft so formed.

While reference is made in the foregoing process and discussion to the cord vein, the same process is equally applicable to the cord artery.

The prosthesis produced according to this improved process is a stronger, more flexible, graft having improved aldehyde crosslinkages between adjacent collagen molecules of the vessel tissue and being more resistant to degradation and the development of aneurysms. It is hypothesized that applying the tanning solution to the cord vessels under cyclic pressure simulating the pulsating systolic pressure that an arterial vessel experiences conditions the cord to the rigors of cyclic pressure. At the same time, the increased pressure forces the gluteraldehyde molecules within the tanning solution to be more active, thus leading to an increase in the formation of aldehyde cross-linkages between adjacent collagen molecules of the cord vessel. The increased pressure also encourages aldehyde bond formation deeper into the vascular surface. The resulting prosthesis is more reliable in terms of performance and longevity. It is essentially free of antigenicity and is resistant to biologic degradation in the form of aneurysmal deterioration, graft degeneration, ectasia or hyperplasia. Late failure of grafts due to these problems are thus reduced.

The umbilical cord vein is treated with tanning agent under cyclic pressure. A continuous flow of tanning agent is provided so that the tanning solution is maintained at a predictable, consistent concentration. The tanning solution may be recycled and/or reconcentrated so that a continuous flow of gluteraldehyde solution at a consistent concentration is maintained.

As discussed supra, umbilical cord vessels have previously been tanned by simply placing the vessel on a mandrel in a tank of tanning solution. Applicants in this invention have improved the tanning process by providing that the tanning agent be applied to both the exterior and interior surfaces of the cord vessel and that the tanning step be conducted under cyclic pressure and flow. Various combinations and permutations of these steps are possible and all are deemed to fall within the scope of this invention.

The umbilical cord is cleaned using known cleaning agents. Gluteraldehyde is then applied to harden the outer surface of the vein, a mandrel is inserted in the center of the vein to establish a minimum bore dimension of the vein and the vein is spun on a lathe to mechanically remove extraneous outer tissue from the outer surface of the vein. In this way, separation of the arteries and the vein occurs and the valves of Hoboken are removed from within the vessel.

The cord vessels are treated with a tanning solution of gluteraldehyde, at concentrations up to 1.0%, at a systolic pressure of 100-200 mm Hg and at a rate of 20 to 30 times/minute. Alternatively, cyclic pressure of 0-200 mm Hg is applied. The process of tanning the cord vessels under cyclic pressure is continued for a total duration of 24 to 36 hours. Note that human systolic pressure is normally up to 150 mm Hg.

The final step in the process of producing arterial prostheses from human umbilical cord vessels is applying an external sleeve-like biodegradable mesh support to the shaped and tanned prosthesis. The mesh support in applicant's prior process described in U.S. Pat. No. 3,974,526 was made of any non-absorbable synthetic material such as Dacron ®, Teflon ®, polyester, polypropylene and Mersilene mesh. The mesh was intended to provide support for the graft and was not meant to be absorbed by it or the recipient host tissue readily. The external supporting mesh contemplated by the present invention, however, is preferably composed of biodegradable polylactic acid or polygalactic acid polymer. These are biodegradable copolymers completely resorbed in vivo by macrophage phagocytosis and hydrolysis. The use of these absorbable materials as a mesh support is more likely to provide a framework for the ingrowth of host fibroblasts. These fibroblasts will then secrete collagen, leading to the formation of a strong fibrous capsule around the tubular prosthesis. Histologic evidence suggests that the quality of host collagen ingrowth is suboptimal with nonabsorbable materials such as polyester or Dacron ® and can be significantly improved with the use of a biodegradable material as an alternative mesh. The biodegradable mesh framework surrounding the arterial prosthesis is exposed to surrounding tissue and permits ingrowth of fibroblasts and endothelial cells resulting in the attachment of the prosthesis to the host cells. At that point, the biodegradable mesh support will be completely absorbed and support for the graft will be provided entirely by host cells.

The new biodegradable mesh could also be used with prostheses made according to prior processes which do not include tanning under cyclic fluid pressure.

Note that Greisler et al ("J. of Vascular Surgery", Vol 3. No. 5 [1986] pages 747-756) indicates that Dacron prostheses inhibit arterial regenerative activity while absorbable polyglycolic acid or polyglactin 910 prostheses stimulate arterial regeneration. It is significant that Greisler et al uses biodegradable polymers as blood vessel substitutes and not as a supporting mesh for a human umbilical cord arterial prosthesis. Greisler's et al's biodegradable prostheses are intended to be absorbed and replaced by arterial regencration. They are not meant to provide support for a biologically derived graft, or to act as a frame for the ingrowth of host collagen so as to attach the prosthesis to the host cells.

BRIEF DESCRIPTION OF THE DRAWINGS

FIG. 1 is an elevation view showing a first embodiment of the new process for treating umbilical cord vessels;

FIG. 2 is a sectional view taken along line 2—2 of FIG. 1;

FIG. 3 is an elevation view showing a second embodiment of the new process; and

FIG. 4 is a sectional view taken along line 4—4 of FIG. 3.

DESCRIPTION OF PREFERRED EMBODIMENT

Example I

A vascular graft may be prepared in accordance with the present invention by cleaning the umbilical cord and removing extraneous tissue from the outer surface of the vessel desired. This is accomplished by setting the cord vein on a lathe and cutting away extraneous tissue from the surface of the vein. Alternatively, the desired vessel, for example the vein, may first be hardened by contacting it with gluteraldehyde and then the hardened vein is set on the lathe and extraneous hardened tissue trimmed.

A mandrel of desired final inside diameter of the prosthesis is then placed in the lumen of the umbilical cord vessel. Tanning agent is applied which causes the vessel to conform to the shape of the mandrel and simultaneously increases the strength of the vessel material. The practice of shrinking a vein or artery onto a mandrel contracts the vessel down to the diameter of the mandrel and has the advantage that any internal irregularities such as the valves of Hoboken are eliminated.

The vein in the human umbilical cord is substantially larger than the arteries. While the vein ranges in size from 4-6 mm in diameter, the artery measures only 1.5-3 mm in diameter. Consequently, where larger segments are desired, veins are used in preference to arteries. Using either an internal mandrel or an external mold, a vein can be distended out to about 1.0 cm internal diameter. The diameter of a human umbilical cord artery can be distended up to about 5 mm and can be collapsed down to about 0.5 mm. Arteries of such small diameter are particularly valuable for replacement of blood vessels in the body.

The mandrel inserted to shape the vessels and remove the valves of Hoboken may be constructed of an inert material which will not react with the graft vessel or chemicals used in the process. For these purposes, glass, silicon, stainless steel or plastic may be used. The mandrel may be straight or curved, solid or hollow, cylindrical or tapered and smooth or perforated

Example II

Referring now to FIGS. 1 and 2, a vascular graft is prepared wherein tanning fluid is applied under cyclic pressure to the exterior surfaces of the cord vessel. A mandrel or stent 2 is inserted within the lumen of the umbilical cord vessel 1. This device, constructed of metal or plastic, is a solid rod and measures 5 mm. in diameter. The umbilical cord vessel 1 on the stent or mandrel 2 is then placed within a chamber 3 defined by walls 3a that is of sufficient length to accommodate the umbilical vessel and is 1 cm. in diameter greater than the outer diameter of the vein on the mandrel. Multiple ports at different levels of this chamber are connected to external pumps 4 that will permit the tanning fluid to be injected under controlled flow and pressure. Note that the tanning agent is applied under cyclic pressure to the outside surfaces of the cord vessel and is compressed against the previously placed intraluminal stent or mandrel.

A tanning solution of gluteraldehyde, at concentrations up to 1.0%, is injected into the chamber under controlled flow. Cyclic pressure of 100-200 mm Hg at a rate of 20 to 30 times/minute is applied for a total duration of 24 to 36 hours. Alternatively, cyclic pressure of 0-200 mm Hg is applied to the tanning solution in the chamber.

Example III

An alternative vascular graft which may be tanned by applying tanning fluid under cyclic pressure from within the graft may also be prepared. See FIGS. 3 and 4. A hollow cannula 6 constructed of metal or plastic, measuring between 2.5 and 3.5 mm in diameter and having multiple perforations in its cylindrical surface is attached to an external pump to allow delivery of the tanning solution at predetermined flow rates and pressure. The cannula is placed within the lumen of the umbilical cord vessel 7 which in turn is then placed in a chamber 8 defined by walls 9 and constructed of metal or plastic, that, when closed, will measure 5.8 mm in diameter and of sufficient length to accommodate the particular length of the umbilical cord vessel. The tanning agent applied under cyclic pressure axially into the cannula, exits via the radially directed perforations against the inner bore surface of the cord. This apparatus permits fluid to be pumped from within the graft and at the same time prevents outward expansion of the graft beyond a total diameter of 5.8 mm.

Tanning solution of gluteraldehyde, at concentrations up to 1.0%, is injected under controlled flow and pressure. Cyclic pressure in the range of 100-200 mm Hg is applied to the tanning solution at a rate of 20 to 30 times/minute for a duration of 24 to 36 hours. Alternatively, cyclic pressure of 0-200 mm Hg is applied to the solution in the chamber.

Example IV

Tanning of the umbilical cord vessel may proceed in a variety of ways. Previously, umbilical cord vascular grafts have been tanned by simply placing the cord vein or artery on a mandrel in a tank of tanning solution. This procedure tans only the exterior surface of the cord vessel. Applicants have found that tanning both the interior and the exterior surfaces of the vein or artery and more particularly, tanning the exterior and interior surfaces under cyclic pressure, leads to an improvement in the aldehyde cross-linkages between adjacent collagen molecules which results in an improved graft more resistant to degredation and aneurysm development.

In one embodiment of applicant's invention, the inner surface of the vein may be tanned by contacting it with gluteraldehyde solution. Alternatively, the vessel may be tanned by contacting the inner surface of the vein with tanning agent under cyclic pressure, as described in EXAMPLE III, supra.

In another embodiment of this invention, only the outer surface of the vein is tanned by contacting the outer surface with tanning agent under cyclic pressure. In another version of this invention, both the inner and outer surfaces of the vein may be tanned with or without cyclic pressure.

In yet another embodiment of this invention, the vein may be treated by contacting the inner surface of the vein with tanning agent after the outer surface has been tanned or vice versa. Alternatively, the inner surface of the vein may be tanned under cyclic pressure and the outer surface of the vein may be tanned at atmospheric pressure and vice versa.

It will thus be seen that certain changes may be made in carrying out the above process without departing from the spirit and scope of the invention. It is intended that all matter contained in the above description and shown in the accompanying drawings be interpreted as illustrative and not in a limiting sense.

What is claimed is:

1. A process for producing a tubular prosthesis for vascular reconstructive surgery from a selected blood vessel of the human umbilical cord, wherein said umbilical cord comprises blood vessels and umbilical cord tissue, said blood vessels comprising a vein and two arteries, the process comprising the steps of:
    a. cleansing the umbilical cord;
    b. separating the two arteries and vein from the umbilical cord tissue and from one another;
    c. removing umbilical cord tissue from the outer surface of said selected blood vessel;
    d. establishing and maintaining a minimum bore dimension of said selected blood vessel by inserting within the bore of said selected blood vessel a mandrel having an outer diameter essentially equal to said minimum bore dimension of said selected blood vessel and a length substantially equal to the length of said selected blood vessel, said selected blood vessel being open at least at one end; and
    e. treating said selected blood vessel by applying tanning agent under cyclic pressure to the outer surface of said selected blood vessel such that said selected blood vessel contracts down to said outer diameter of said mandrel.

2. The process according to claim 1, comprising the further step of treating said selected blood vessel with an antithrombogenic agent after said tanning step.

3. The process according to claim 1, comprising the further step of applying a sleeve-like biodegradable mesh support externally and generally coaxially along the length of the tanned selected blood vessel.

4. A process according to claim 1, wherein the tanning agent used in step (e) is gluteraldehyde at a concentration in the range of about 0.15% to 1.0%.

5. A process according to claim 1, wherein treating said selected blood vessel comprises flowing the tanning agent under said cyclic pressure while it is in contact with said selected blood vessel.

6. A process according to claim 1, wherein the cyclic pressure is in the range of about 0 to 200 mm Hg.

7. A process according to claim 1, wherein treating said vein comprises applying said cyclic pressure at a rate of 20 to 30 times/minute.

8. A process according to claim 1, step (e), wherein said selected blood vessel is treated with a tanning agent under cyclic pressure for a time period in the range of 24 to 36 hours.

9. A process according to claim 3, wherein the biodegradable mesh support is polylactic acid or polygalactic acid polymer.

10. A process according to claim 1, wherein the mandrel inserted in step (d) is a solid rod measuring 5 mm in diameter.

11. A tubular prosthesis made according to the process of claim 1 suitable for repairing, replacing or augmenting a vein or artery of a human, primate or mammal body, said prosthesis comprising a selected blood vessel of a human, primate or mammal umbilical cord that has been separated from the outer umbilical cord tissue, shaped on a mandrel and tanned with a tanning agent applied under cyclic pressure.

12. The tubular prosthesis of claim 11 wherein a biodegradable mesh support is fitted coaxially about and along the length of said tanned selected blood vessel.

13. A process for producing a tubular prosthesis for vascular reconstructive surgery from a selected blood vessel of the human umbilical cord, wherein said umbilical cord comprises blood vessels and umbilical cord tissue, said blood vessels comprising a vein and two arteries, the process comprising the steps of:
   a. cleansing the umbilical cord;
   b. separating the two arteries and vein from the umbilical cord tissue and from one another;
   c. removing umbilical cord tissue from the outer surface of said selected blood vessel;
   d. establishing and maintaining a minimum bore dimension of said selected blood vessel by inserting within the bore of said selected blood vessel a mandrel having an outer diameter essentially equal to said minimum bore dimension of said selected blood vessel;
   e. positioning and maintaining tanning fluid around the selected blood vessel to be tanned; and
   f. treating said selected blood vessel by applying tanning agent under cyclic pressure to the outer surface of said selected blood vessel such that said selected blood vessel contracts down to said outer diameter of said mandrel.

14. A process for producing a tubular prosthesis for vascular reconstructive surgery from a selected blood vessel of the human umbilical cord, wherein said umbilical cord comprises blood vessels and umbilical cord tissue, said blood vessels comprising a vein and two arteries, the process comprising the steps of:
   a. cleansing the umbilical cord;
   b. separating the two arteries and vein from the umbilical cord tissue and from one another;
   c. removing umbilical cord tissue from the outer surface of said selected blood vessel;
   d. establishing and maintaining a predetermined inner diameter of said selected blood vessel along its entire circumferential inner surface; and
   e. maintaining said predetermined inner diameter while applying tanning agent under cyclic pressure to the outer surface of said selected blood vessel such that said selected blood vessel contracts down to said outer diameter of said mandrel.

15. A process according to claim 14 wherein a mandrel having an outer diameter essentially equal to said predetermined inner diameter of said blood vessel is inserted within the bore of said selected blood vessel in step (d) to establish and maintain a predetermined inner diameter of said vessel.

16. A process for tanning the outer surface of a selected blood vessel of an umbilical cord under cyclic pressure, said tanned vessel having utility as a prosthesis for vascular reconstructive surgery, comprising the steps of:
   a. establishing and maintaining a predetermined inner dimension of said selected blood vessel along its entire circumference; and
   b. treating said selected blood vessel by applying tanning agent under cyclic pressure to the outer surface of said selected blood vessel.

17. A process for producing a tubular prosthesis for vascular reconstructive surgery from a selected blood vessel of the human umbilical cord, wherein said umbilical cord comprises blood vessels and umbilical cord tissue, said blood vessels comprising a vein and two arteries, the process comprising the steps of:
   a. cleansing the umbilical cord;
   b. separating the two arteries and vein from the umbilical cord tissue and from one another;
   c. removing umbilical cord tissue from the outer surface of said selected blood vessel;
   d. establishing and maintaining a minimum bore dimension of said selected blood vessel by inserting within the bore of said selected blood vessel a mandrel having an outer diameter essentially equal to said minimum bore dimension of said selected blood vessel and a length substantially equal to the length of said selected blood vessel, said selected blood vessel being open at both ends; and
   e. treating said selected blood vessel by applying tanning agent under cyclic pressure to the outer surface of said selected blood vessel such that said selected blood vessel contracts down to said outer diameter of said mandrel.

18. A process for producing a tubular prosthesis for vascular reconstructive surgery form a selected blood vessel of the human umbilical cord, wherein said umbilical cord comprises blood vessels and umbilical cord tissue, said blood vessels comprising a vein and two arteries, the process comprising the steps of:
   a. cleansing the umbilical cord;
   b. separating the two arteries and vein from the umbilical cord tissue and from one another;
   c. removing umbilical cord tissue from the outer surface of said selected blood vessel;
   d. establishing and maintaining a minimum bore dimension of said selected blood vessel by inserting within the bore of said selected blood vessel a mandrel having an outer diameter essentially equal to said minimum bore dimension of said selected blood vessel and a length substantially equal to the length of said selected blood vessel, said selected blood vessel being open at least at one end; and
   e. treating said selected blood vessel by applying tanning agent under cyclic pressure to the outer surface of said selected blood vessel such that said selected blood vessel contracts down to said outer diameter of said mandrel, wherein said cyclic pressure to which said selected blood vessel is subjected is greater than the physiologic range when said selected blood vessel is implanted.

19. A process according to claim 18 wherein said cyclic pressure is in the range of 120 nm to 200 mm Hg.

20. A process for producing a tubular prosthesis for vascular reconstructive surgery from a selected blood vessel of the human umbilical cord, wherein said umbilical cord comprises blood vessels and umbilical cord tissue, said blood vessels comprising a vein and two arteries, the process comprising the steps of:
   a. cleansing the umbilical cord;
   b. separating the two arteries and vein from the umbilical cord tissue and from one another;
   c. removing umbilical cord tissue from the outer surface of said selected blood vessel;

d. establishing and maintaining a minimum bore dimension of said selected blood vessel by inserting within the bore of said selected blood vessel a mandrel having an outer diameter essentially equal to said minimum bore dimension of said selected blood vessel and a length substantially equal to the length of said selected blood vessel, said selected blood vessel being open at both ends; and e. treating said selected blood vessel by applying tanning agent under cyclic pressure to the outer surface of said selected blood vessel such that said selected blood vessel contracts down to said outer diameter of said mandrel, wherein said cyclic pressure to which said selected blood vessel is subjected is greater than the physiologic range when said selected blood vessel is implanted.

* * * * *